United States Patent
Li et al.

(10) Patent No.: US 10,495,588 B2
(45) Date of Patent: Dec. 3, 2019

(54) BOREHOLE SIGNAL REDUCTION FOR A SIDE-LOOKING NMR LOGGING TOOL USING A MAGNET ASSEMBLY

(71) Applicant: Halliburton Energy Services, Inc, Houston, TX (US)

(72) Inventors: Lilong Li, Humble, TX (US); Rebecca Jachmann, Houston, TX (US); Arcady Reiderman, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/506,038

(22) PCT Filed: Nov. 12, 2014

(86) PCT No.: PCT/US2014/065265
§ 371 (c)(1),
(2) Date: Feb. 23, 2017

(87) PCT Pub. No.: WO2016/076861
PCT Pub. Date: May 19, 2016

(65) Prior Publication Data
US 2017/0307552 A1 Oct. 26, 2017

(51) Int. Cl.
*G01N 24/08* (2006.01)
*G01R 33/38* (2006.01)
*G01V 3/32* (2006.01)
(52) U.S. Cl.
CPC ....... *G01N 24/081* (2013.01); *G01R 33/3808* (2013.01); *G01V 3/32* (2013.01)

(58) Field of Classification Search
None
See application file for complete search history.

(56) References Cited

U.S. PATENT DOCUMENTS

| | | |
|---|---|---|
| 5,557,201 A | 9/1996 | Kleinberg et al. |
| 5,834,936 A | 11/1998 | Taicher et al. |
| 6,133,734 A | 10/2000 | McKeon |
| 6,291,995 B1 | 9/2001 | Speier et al. |
| 6,348,792 B1 | 2/2002 | Beard et al. |
| 6,429,654 B1 | 8/2002 | Itskovich et al. |
| 6,445,180 B1 | 9/2002 | Reiderman et al. |
| 6,489,763 B1 | 12/2002 | Goswami et al. |
| 6,525,535 B2 | 2/2003 | Reiderman et al. |
| 6,580,273 B2 | 6/2003 | Reiderman et al. |
| 2002/0125885 A1 | 9/2002 | Reiderman et al. |
| 2003/0210050 A1 | 11/2003 | Prammer et al. |
| 2004/0130324 A1 | 7/2004 | Edwards |
| 2007/0222444 A1 | 9/2007 | Reiderman |

OTHER PUBLICATIONS

International Search Report and The Written Opinion of the International Search Authority, or the Declaration, dated Jul. 23, 2015, PCT/US2014/065254, 15 pages, ISA/KR.

(Continued)

*Primary Examiner* — Xiaoyun R Xu
(74) *Attorney, Agent, or Firm* — Haynes and Boone, LLP (57) ABSTRACT

A side-looking Nuclear Magnetic Resonance ("NMR") logging tool is designed to reduce and/or eliminate a borehole signal. The logging tool includes a magnet assembly having at least two magnets with magnetizations in different directions, thus resulting in a net magnetization that reduces the borehole signal.

6 Claims, 4 Drawing Sheets

(56) References Cited

OTHER PUBLICATIONS

International Search Report and The Written Opinion of the International Search Authority, or the Declaration, dated Jul. 23, 2015, PCT/US2014/065260, 12 pages, ISA/KR.
International Search Report and The Written Opinion of the International Search Authority, or the Declaration, dated Jul. 23, 2015, PCT/US2014/065265, 15 pages, ISA/KR.
Extended European Search Report issued for EP Appl. No. 14905734.1, dated Nov. 6, 2017, 7 pages.

| length of antenna | B1 at 3 inches DOI in the front (B1_front, in Gauss) | B1 at B0 isoline in the back (B1_back, in Gauss) | B1_back/B1_front (%) |
|---|---|---|---|
| Inf (2D) | 0.0171 | 0.00247 | 14.4 |
| 36" | 0.0182 | 0.00217 | 11.9 |
| 24" | 0.0201 | 0.00190 | 9.5 |
| 12" | 0.0249 | 0.00123 | 4.9 |

BOREHOLE SIGNAL REDUCTION FOR A SIDE-LOOKING NMR LOGGING TOOL USING A MAGNET ASSEMBLY

PRIORITY

The present application is a U.S. National Stage patent application of International Patent Application No. PCT/US2014/065265, filed on Nov. 12, 2014, the benefit of which is claimed and the disclosure of which is incorporated herein by reference in its entirety.

FIELD OF THE DISCLOSURE

The present disclosure generally relates to logging tools and, more particularly, to methods for reducing borehole signals for side-looking Nuclear Magnetic Resonance ("NMR") logging tools.

BACKGROUND

A variety of techniques have been used in determining the presence quantities of hydrocarbons (oil and gas) in earth formations. One such technique involves the use of NMR logging tools for determining, among other things porosity, hydrocarbon saturation and permeability of the rock formations. The NMR logging tools are utilized to excite the nuclei of the fluids in the geological formations in the vicinity of the wellbore so that certain parameters such as spin density, spin-lattice relaxation time (generally referred to in the art as "T1"), and spin-spin relaxation time (generally referred to as "T2") of the geological formations can be estimated. From such measurements, porosity, permeability, and hydrocarbon saturation are determined, which provides valuable information about the make-up of the geological formations and the amount of extractable hydrocarbons.

A conventional "side-looking" NMR tool is sensitive to NMR excitation on one side of the tool and less sensitive to NMR excitation on the other side. The more sensitive side of the tool is typically pressed against the side wall of a borehole adjacent a formation, thereby providing minimum separation between the NMR tool's radio frequency ("RF") field generating assembly and the formation volume of NMR investigation. The less sensitive side of the tool is thus exposed to the borehole, which gives rise to the issue of borehole signal whereby the NMR signal from the borehole tends to erroneously contribute to the received NMR signal (i.e., "total signal" as referred to herein) from the volume of interest.

A variety of conventional techniques have been utilized to combat the issue of the borehole signal. In one example, a side looking NMR tool design includes a dipole RF antenna displaced toward the formation and a single permanent magnet, having a single magnetization direction, placed toward the back of the tool. However, for such a configuration, the signal from borehole will still be unacceptably large for larger boreholes. To solve this problem, other approaches have utilized a tool having an active RF spoiler design where a spoiler in the back, possessing a dipole moment opposite to that of the front antenna, spoils the borehole signal to an acceptable level. However, a spoiler implementation introduces a high level of complexity in terms of building and testing of the tool, as well as reliability issues.

Therefore, there is a need in the art to provide alternative, reliable and less complex NMR logging tools capable of eliminating and/or reducing the borehole signal to an acceptable amount.

DESCRIPTION OF ILLUSTRATIVE EMBODIMENTS

Illustrative embodiments and related methods of the present disclosure are described below as they might be employed for reducing the borehole signals for side-looking NMR tools. In the interest of clarity, not all features of an actual implementation or methodology are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies of the disclosure will become apparent from consideration of the following description and drawings.

As described herein, methods and related embodiments of the present disclosure are directed to the reduction of the borehole signal for a side-looking NMR logging tool. In a first generalized embodiment of the present disclosure, a side-looking NMR logging tool includes a magnetic assembly to generate a static magnetic field, and an RF transceiver antenna to induce an RF field into the volume of interest and to receive corresponding total signals from the volume of interest. The axial extent of the RF transceiver antenna has a length selected to reduce a borehole signal.

In a second generalized embodiment of the present disclosure, a side-looking NMR logging tool includes an RF transceiver antenna to induce an RF field into a volume of interest and thereby receive a corresponding total signal from the volume of interest. The NMR logging tool further includes a magnet assembly having at least two magnets with magnetizations in different directions. As a result, the static magnetic field produced by the magnet assembly acts to reduce the borehole signal by shifting the sensitive area in the back of the tool further away from the tool and, thus, further out of the borehole.

In a third generalized method of the present disclosure, an NMR logging tool is deployed into a wellbore to conduct logging operations. A static magnetic field is induced into a volume of interest to thereby polarize the nuclear spin within the volume of interest. An RF excitation pulse is then induced into the volume of interest to rotate the nuclear spin. The RF refocusing pulse is induced into the volume of interest to generate a spin echo. The flipping angle of the RF refocusing pulse is reduced to less than 180 degrees. Reducing the flipping angle of the refocusing pulse to less than 180 degrees has a disproportionate reduction effect on the total signal received from the volume of interest via the reduction effect on the borehole signal being much larger than the formation signal. Thus, the borehole signal as a percentage of the total signal will be reduced. In an alternate embodiment, the same effect is achieved by reducing the excitation pulse to less than 90 degrees. Accordingly, various embodiments of the present disclosure minimize borehole signals in NMR logging for side-looking tools.

Figure 1:
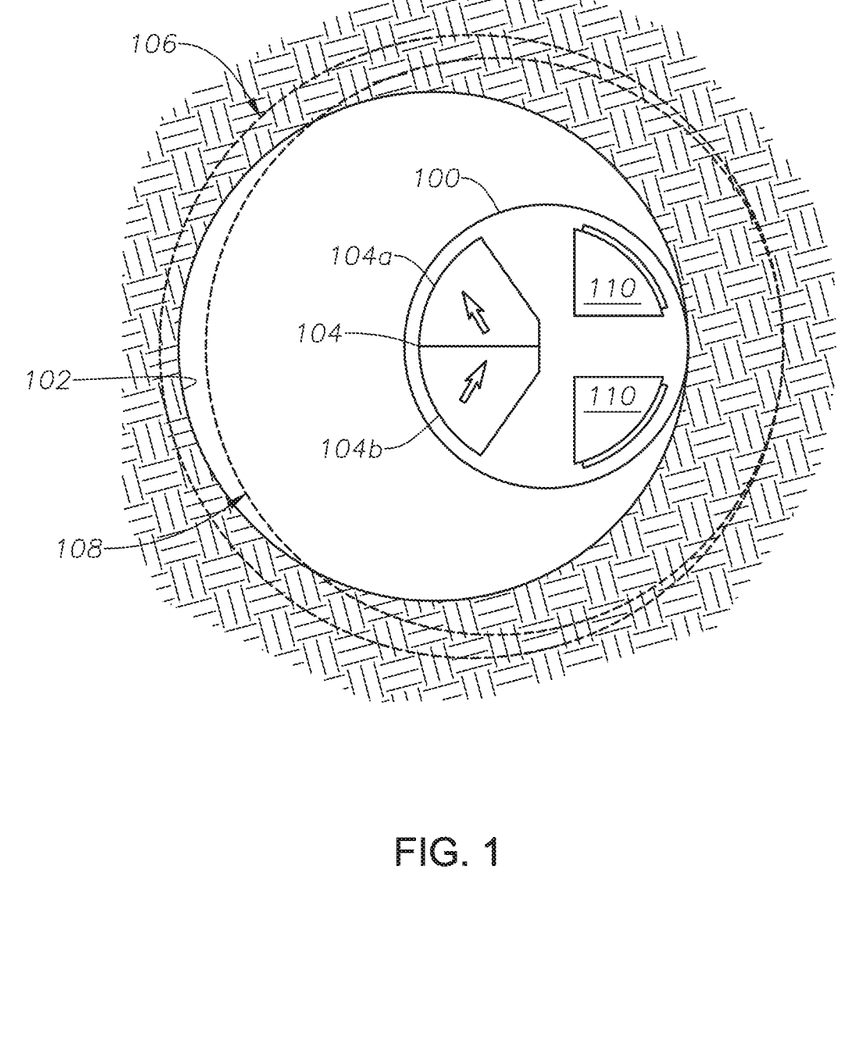
FIG. 1 illustrates the magnetic field distributions for a side-looking NMR logging tool, according to an illustrative embodiment of the present disclosure.

FIG. 1 illustrates the magnetic field distributions for a side-looking NMR logging tool, according to an illustrative embodiment of the present disclosure. In FIG. 1, a cross-section of side-looking NMR logging tool 100 is shown deployed along a wellbore 102. In this embodiment, NMR logging tool 100 includes a magnet assembly 104 that generates static magnetic field 106 (illustrated as a magnetic field isoline) which extends out into the volume of interest surrounding wellbore 102. As used herein, B is the symbol used to represent magnetic fields. The primary magnetic field emanating from magnet assembly 104 is B0. The other magnetic field emanating from RF transceiver antenna 110 is B1 (an alternating magnetic field).

Magnet assembly 104 includes a first and second magnet 104a and 104b, respectively. NMR logging tool 100 further includes RF transceiver antenna 110 that includes a soft magnetic core and antenna wire at the right of tool 100. RF transceiver antenna 110 induces an RF field, B1, into the volume of interest surrounding the borehole of wellbore 102 and receives the corresponding total signals from the volume, as will be understood by those ordinarily skilled in the art having the benefit of this disclosure.

In this illustrative embodiment, NMR logging tool 100 is positioned against the right side of the wall of wellbore 102. Magnet assembly 104 is positioned on a second side (i.e., back side) of NMR logging tool 100, while RF transceiver antenna 110 is positioned on the first side (i.e., front side), which is opposite of the second side, of NMR logging tool 100. As indicated by the boldened arrows, first and second magnets 104a,b have different directions of magnetization which produces static magnetic field 106. Because of the differing magnetization directions of magnets 104a,b, the resulting static magnetic field 106 is shifted outside the borehole of wellbore 102, thus reducing the borehole signal. In this example, first magnet 104a is polarized in the upper-left direction, while the magnetization of second magnet 104b is tilted in upper-right direction. Alternatively, however, first magnet 104a may be polarized in the downward-right direction, while second magnet 104b may be polarized in the downward-left direction. In yet other examples, For example, first magnet 104a may be tilted 10-20 degrees in relation to second magnet 104b. Those ordinarily skilled in the art having the benefit of this disclosure realize there are a variety of tilt orientations which may be utilized without departing from the spirit and teachings of the present disclosure.

Still referring to FIG. 1, magnetic field isoline 108 illustrates the static magnetic field produced using magnet assemblies in which both magnets are polarized in the same direction, and is shown to further illustrate the novel aspects of the present disclosure. As can be seen, static magnetic field 106 produced using this embodiment of the present disclosure is shifted to the left when compared to the static magnetic field 108. As a result, static magnetic field 108 includes more of the borehole signal than static magnetic field 106. Therefore, regardless of which tilt orientation is utilized in the present disclosure, the titled magnetic assembly 100 shifts the center of the magnet dipole (static magnetic field 106) to the left, thus reducing the borehole signal for the same depth of investigation when compared to tools having all magnets polarized in the upright, or same, direction.

To further explain the embodiment of FIG. 1, the effective center of the static magnetic field B0 (106) is shifted to reduce the borehole signal. As illustrated in FIG. 1, for the same depth of investigation ("DOI") in the front (first side) of NMR logging tool 100, the further the B0 magnetic field isoline 106 moves to the left, the higher the contrast between the RF field strength (B1) in the back as compared to that in the front of tool 100. As the RF field strength (B1) in the back of tool 100 is weakened relative to that in the front, the net effect is: 1) a smaller tipping angle for nuclei in the back of tool 100, which results in a smaller processing nuclear magnetic moment from the back; and 2) a lowered sensitivity for transceiver antenna 110 to the NMR signal (i.e., total signal) from that area. Both of these effects contribute to a smaller borehole signal. For some smaller bore holes, as the one shown in FIG. 1, the center of the B0 field 106 is pushed far enough back that a signal does not come from the borehole anymore. When the same tool is placed in larger boreholes, however, the result is a smaller borehole signal.

As will be understood by those ordinarily skilled in the art having the benefit of this disclosure, in order to shift the effective center of the B0 field 106, a magnet may be positioned as far left as possible in the tool (as shown in FIG. 1). In certain embodiments of the current disclosure, the effective center of static magnetic field 106 is shifted even further by tilting the magnetic field orientation as illustrated in FIG. 1. As described above, in certain illustrative embodiments, a tilting of 5 degrees reduces the borehole signal from 1.23 p.u. (in the case of regular straight field orientation) to 0.9 p.u., with the same 12" antenna.

Although static magnetic field 106 is shown completely outside the borehole of wellbore 102, such a borehole reduction is not required. For example, in some applications, the sought borehole signal reduction may not be as stringent, and therefore it may not be necessary for static magnetic field 106 to be pushed completely outside the borehole.

Figure 2:
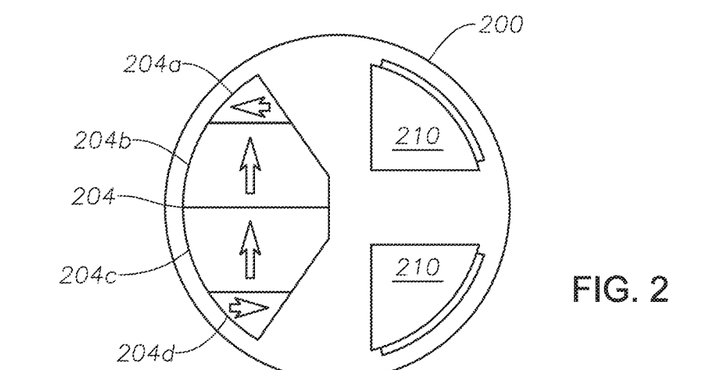
FIG. 2 illustrates an NMR logging tool 200, according to an alternative embodiment of the present disclosure.

The tilting of the net magnetization may be achieved in a variety of ways. FIG. 2 illustrates an NMR logging tool 200, according to an alternative embodiment of the present disclosure. Side-looking NMR logging tool 200 operates the same as tool 100 wherein magnet assembly 204 has a tilted net magnetization which produces a static magnetic field that reduces the borehole signal. However, in logging tool 200, magnet assembly 204 includes first magnet 204a, second magnet 204b, third magnet 204c and fourth magnet 204d. As shown, first magnet 204a includes a magnetization in a first direction (to the left in this illustration); second magnet 204b is positioned adjacent to first magnet 204a and includes a magnetization in a second direction orthogonal to the first direction; third magnet 204c is positioned adjacent to second magnet 204b and has a magnetization is the second direction (same as second magnet 204b); and fourth magnet 204d is positioned adjacent third magnet 204c and has a magnetization is a third direction opposite the first magnetization direction of first magnet 204a. When each magnetization of magnets 104a-d is combined, magnet assembly 204 induces a static magnetic field shifted along the borehole in such a way to reduce and/or remove the borehole signal.

In yet another illustrative embodiment of the present disclosure, the design of a side-looking NMR logging tool takes advantage of the three-dimensional ("3D") effect of the RF dipole. As will be understood by those ordinarily skilled in the art having the benefit of the present disclosure, the magnetic field generated by a 3D RF dipole will decay faster than that of a 2D RF dipole ($\alpha\ 1/r^3$ for 3D far field as compared to $\alpha\ 1/r^2$ for 2D far field). Here, as illustrated in FIGS. 1-2, the signal coming from the front (right side) of NMR logging tool 100/200 is located much closer to RF transceiver antenna 110,210 than the signal coming from the back. Therefore, by replacing a 2D RF dipole (a very long transceiver antenna) with a 3D RF dipole (a very short transceiver antenna), relative to the B1 oscillating magnetic field strength at the DOI in the front to tool 100,200, B1 in the back will be much weaker.

In certain embodiments, for example, the very short antenna refers to an antenna having an axial extent not much longer than the distance from the antenna to the sensitive volume of interest on the back of tool 100,200. In terms of NMR, the tipping angle for nuclei in the back will be much smaller, which in turn reduces the sensitivity of transceiver antenna 110,210 for the signal coming from that back area. Accordingly, the resulting effect is a much smaller borehole signal. In certain other embodiments, the length of RF transceiver antenna 110,210 may be selected to reduce the borehole signal to less than 1 p.u. (porosity unit) of the total signal in a borehole approximately 12.25 inches in diameter. As defined herein, porosity unit refers to the percentage of signal to the total signal when the formation is 100% water. In another embodiment, the length of RF transceiver antenna 110,210 is selected to reduce the borehole signal to less than 0.5 p.u. of the total signal in an approximately 8.5 inch borehole.

Figure 3:
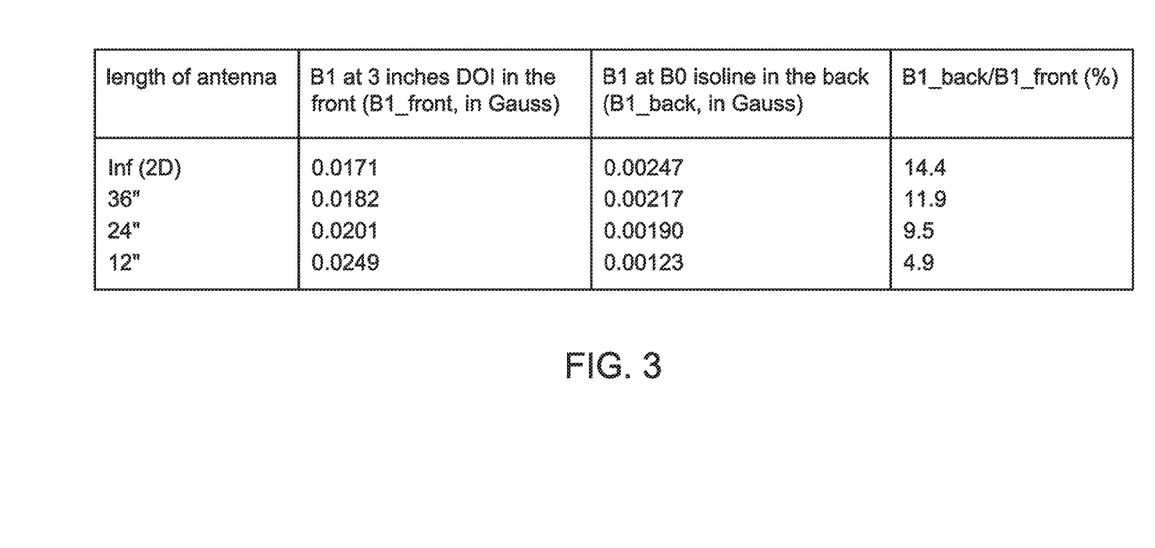
FIG. 3 is a table showing simulation results for B1 in the front and back for an illustrative side-looking NMR logging tool described herein.
Figure 4:
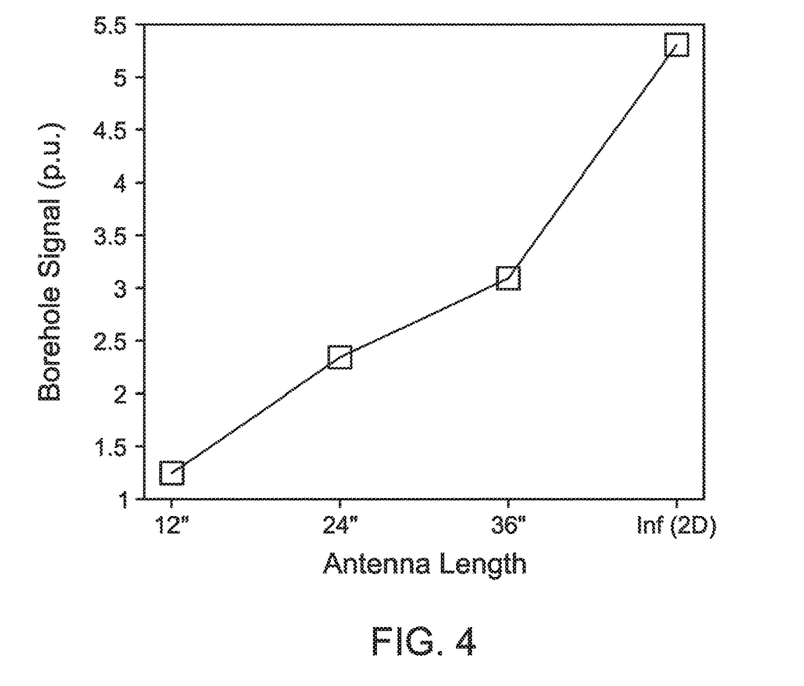
FIG. 4 is a graph showing the borehole signal with respect to various corresponding illustrative antenna lengths.

FIG. 3 is a table showing simulation results for B1 in the front and back for an illustrative side-looking NMR logging tool described herein, and the ratio between them. The comparison of B1 in the back and front is for the same excitation band in the same B0 isoline. As can be seen, while B1 in the front increases because, in the radial direction, the 3D dipole is stronger than the 2D dipole, B1 in the back decreases because of faster decay with respect to distance for a 3D dipole. As a result, the graph of FIG. 4 presents the borehole signal with various corresponding illustrative antenna lengths. A clear trend can be seen as the antenna length is reduced, thus turning from a 2D RF dipole gradually into a 3D RF dipole. Accordingly, in certain embodiments, the axial extent of RF transceiver antenna 110,210 may be between approximately 10-36 inches.

In yet another illustrative method of the present disclosure, the flipping angle of refocusing pulses (e.g., Carr-Purcell-Meiboom-Gill ("CPMG")) is reduced in order to minimize the borehole signal. As will be understood by those ordinarily skilled persons described herein, an NMR tool generates a static magnetic field B0 in the vicinity of the wellbore, and an oscillating field B1 in a direction perpendicular to B0. This oscillating field is usually applied in the form of short duration pulses. The effect of the B0 field is the polarization of the magnetic moments of nuclei parallel to the static field and the purpose of the B1 field is to rotate the magnetic moments by an angle $\theta$ controlled by the duration, $t_p$, and the amplitude |B1| of the oscillating pulse. For NMR logging, the most common sequence is the Carr-Purcell-Meiboom-Gill ("CPMG") sequence that can be expressed as $$P90\text{-}TE/2\text{-}(P180\text{-}TE/2\text{-}ACQ\text{-}TE/2)_n, \qquad \text{Eq. (1)},$$

where P90 represents the 90 degree excitation pulse, P180 is the 180 degree refocusing pulse, TE/2 is the half inter-echo spacing, ACQ is the spin echo acquisition, and n is the looping n times. When the refocusing pulse is adjusted away from 180 degrees, with no consideration to the spin-spin relaxation (T2) or spin-lattice relaxation (T1), the spin echo amplitude will reach a so-called pseudo steady state after a few echoes, and the amplitude is $M_0 \sin(\theta/2)$, where $M_0$ is the total spin magnetization and $\theta$ is the flipping angle of the refocusing pulse. It can also be noted that the derivative of such an amplitude with respect to $\theta$ is proportional to $\cos(\theta/2)$.

Therefore, in certain illustrative methods of the present disclosure, the flipping angle for the area in front of the tool is reduced away from the regular 180 degrees. The resulting change of echo amplitude from that area will be small ($\cos(\theta/2) \approx 0$ when $\theta \approx 180°$). For the area in the back of the tool, however, since the spins there are severely under-rotated, the reduction in echo amplitude will be more significant when the flipping angle is proportionally reduced ($\cos(\theta/2) \approx 1$ when $\theta \approx 0°$). Thus, in certain embodiments, by reducing the flipping angle of the refocusing pulse (or the excitation pulse), the signal received from the back of the tool is disproportionately affected and, thereby, results in a reduced borehole signal. During testing of embodiments of the present disclosure, spin dynamics simulations showed that if the flipping angle of the refocusing pulse is reduced to 135 degrees, for example, the signal in the front of the tool will be reduced by less than 5%, while the signal in the back will be reduced by more than 30%. As a result, the borehole signal is greatly reduced. Note also that in one or more alternative embodiments, this same effect may be achieved by reducing the excitation pulse to less than 90 degrees.

Figure 5:
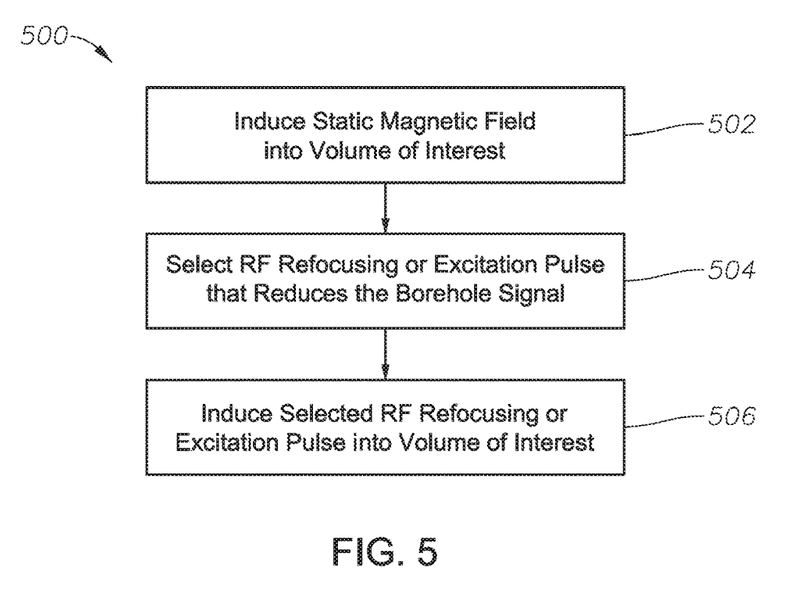
FIG. 5 is a flow chart of a method for reducing the borehole signal through manipulation of flipping angles, according to certain illustrative methods of the present disclosure.

Therefore, in a generalized method and with reference to the flow chart 500 of FIG. 5, a downhole logging tool is deployed into a wellbore and a static magnetic field is induced into the volume of interest using the magnet assembly to thereby polarize nuclear spin, at block 502. At block 504, processing circuitry of the logging tool selects an RF refocusing pulse or RF excitation pulse which will reduce the borehole signal as described above. At block 506, the selected pulse is then induced into the volume of interest, whereby the total signal is received having the reduced and/or eliminated borehole signal. In certain methods, the flipping angle of the RF refocusing pule or RF excitation pulse is reduced to less than 90 degrees, while in other methods the flipping angle is reduced to an angle less than an angle in which a maximum total signal is generated.

Figure 6:
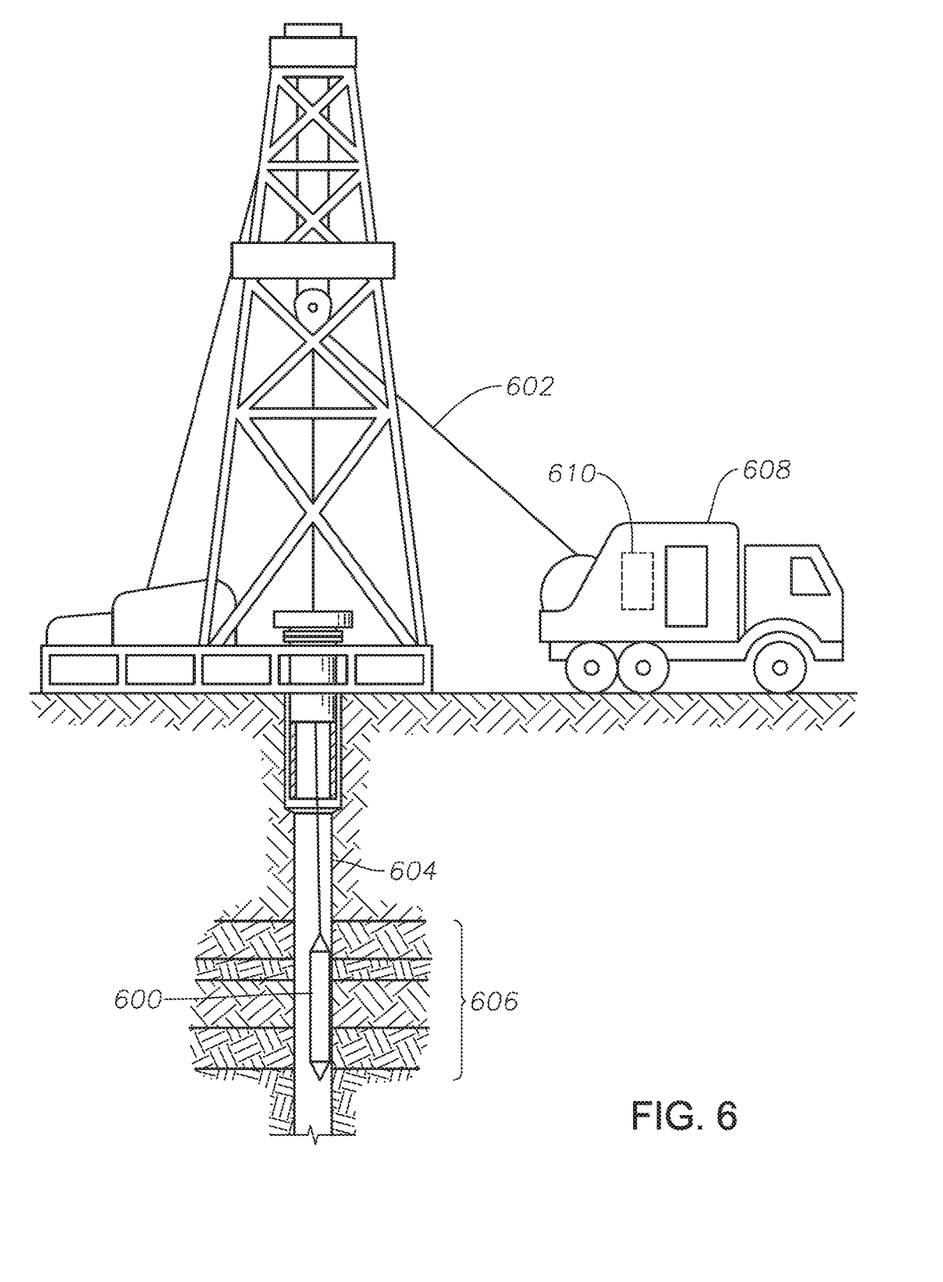
FIG. 6 illustrates an embodiment of the present disclosure whereby a side-looking NMR logging tool is utilized in a wireline application.

FIG. 6 illustrates an embodiment of the present disclosure whereby a side-looking NMR logging tool is deployed in a wireline application. Note, however, that in alternative applications, the logging tools described herein may also be utilized in logging-while-drilling ("LWD") or measurement-while-drilling ("MWD") assemblies, or other desired downhole applications. Nevertheless, with reference to FIG. 5, NMR logging tool 600 embodies one or more of the embodiments and methods described herein. NMR logging tool 600 has been suspended along formation layers 606 by a cable 602 having conductors for transporting power to NMR logging tool 600 and telemetry to/from NMR logging tool 600 and the surface.

In such a deployment, NMR logging tool 600 performs logging operations as desired while reducing the borehole signal as described herein. Once the desired logging data has been acquired, the resulting signals may be saved to a memory disk onboard NMR logging tool 600 and processed in-situ using circuitry onboard tool 600, or transmitted to the surface via cable 602 for well site processing. A logging facility 608 collects measurements from NMR logging tool 600, and may include circuitry 610 for processing and storing the measurements received from NMR logging tool 600.

As stated, in certain embodiments, the methods described above may be performed by processing circuitry onboard the NMR logging tool or located at some remote location. In either case, such processing circuitry would comprises a signal processor, communications module and other circuitry necessary to achieve the objectives of the present disclosure, as will be understood by those ordinarily skilled in the art having the benefit of this disclosure. In addition, it will also be recognized that the software instructions necessary to carry out the objectives of the present disclosure may be stored within storage located within the processing circuitry or loaded into that storage from a CD-ROM or other appropriate storage media via wired or wireless methods. If the processing circuitry is remotely located, a suitable wired or wireless communications link may provide a medium of communication between the processing circuitry and the logging tool. Alternatively, however, the communications link may be an electromagnetic device of suitable frequency, or other methods including acoustic communication and like devices.

Accordingly, the illustrative embodiments and methods described herein provide alternate ways in which to reduce the borehole signal for a side-looking NMR logging tool. As a result, more reliable and less complex NMR logging tools are realized.

Embodiments and methods described herein further relate to any one or more of the following paragraphs:

1. A side-looking nuclear magnetic resonance ("NMR") logging tool, comprising a magnet assembly to generate a static magnetic field in a volume of interest, the magnet assembly comprising at least two magnets having different directions of magnetization such that the static magnetic field reduces a borehole signal; and a radio frequency ("RF") antenna to induce an RF field into the volume of interest and to receive corresponding total signals from the volume of interest.

2. A side-looking NMR logging tool as defined in paragraph 1, wherein the magnet assembly comprises a first magnet comprising a magnetization in a first direction; and a second magnet comprising a magnetization in a second direction which is tilted in relation to the first direction.

3. A side-looking NMR logging tool as defined in paragraphs 1 or 2, wherein the second direction is a tilted at an angle of 10-20 degrees in relation to the first direction.

4. A side-looking NMR logging tool as defined in any of paragraphs 1-3, wherein the magnet assembly comprises a first magnet comprising a magnetization in a first direction; a second magnet positioned adjacent the first magnet, the second magnet comprising a magnetization in a second direction orthogonal to the first direction; a third magnet positioned adjacent the second magnet, the third magnet comprising a magnetization in the second direction; and a fourth magnet positioned adjacent the third magnet, the fourth magnet comprising a magnetization in a third direction opposite the first direction.

5. A side-looking NMR logging tool as defined in any of paragraphs 1-4, wherein the RF antenna is positioned near a front side of the NMR logging tool; and the magnet assembly is positioned near a back side of the NMR logging tool opposite the RF antenna.

6. A side-looking NMR logging tool as defined in any of paragraphs 1-5, wherein the RF antenna is a three-dimensional ("3D") RF dipole.

7. A method for nuclear magnetic resonance ("NMR") logging, the method comprising deploying a logging tool into a wellbore, the logging tool having a radio frequency ("RF") antenna and a magnet assembly; generating a first static magnetic field using a first magnet of the magnet assembly, the first magnet having a magnetization in a first direction; generating a second static magnetic field using a second magnet of the magnet assembly, the second magnet having a magnetization in a second direction different from the first direction; combining the first and second static magnetic fields to reduce a borehole signal from a total signal of the volume of interest; and receiving the total signal from the volume of interest using the RF antenna.

8. A method as defined in paragraph 7, wherein generating the second static magnetic field comprises tilting the magnetization of the second static magnetic field in relation to the first direction.

9. A method as defined in paragraphs 7 or 8, wherein generating the second static magnetic field comprises generating the second static magnetic field to have a magnetization in the second direction which is orthogonal to the first direction, the method further comprising: generating a third static magnetic field using a third magnet having a magnetization in the second direction; and generating a fourth static magnetic field using a fourth magnet having a magnetization in a third direction opposite the first direction, wherein combining the first and second static magnetic fields further comprises combining the third and fourth static magnetic fields to reduce the borehole signal.

10. A method to design a side-looking nuclear magnetic resonance ("NMR") logging tool, comprising selecting a magnet assembly to generate a static magnetic field in a volume of interest, the magnet assembly being configured to reduce a borehole signal; and selecting a radio frequency ("RF") antenna to induce an RF field into the volume of interest and to receive corresponding total signals form the volume of interest.

11. A method as defined in paragraph 10, wherein the magnet assembly is selected to comprise at least two magnets having different directions of magnetization such that the static magnetic field reduces a borehole signal.

12. A method as defined in paragraphs 10 or 11, wherein the magnet assembly is selected to comprise a first magnet comprising a magnetization in a first direction; and a second magnetic comprising a magnetization in a second direction which is tilted in relation to the first direction.

13. A method as defined in any of paragraphs 10-12, wherein the second direction is selected as a tilt angle in relation to the first direction.

14. A method as defined in any of paragraphs 10-13, wherein the magnet assembly is selected to comprise a first magnet comprising a magnetization in a first direction; a second magnet positioned adjacent the first magnet, the second magnet comprising a magnetization in a second direction orthogonal to the first direction; a third magnet positioned adjacent the second magnet, the third magnet comprising a magnetization in the second direction; and a fourth magnet positioned adjacent the third magnet, the fourth magnet comprising a magnetization in a third direction opposite the first direction.

15. A method as defined in any of paragraphs 10-14, wherein the RF antenna is positioned near a first side of the NMR logging tool; and the magnet assembly is positioned near a second side of the NMR logging tool opposite the RF antenna, wherein the second side is opposite the first side.

16. A method as defined in any of paragraphs 10-15, wherein the RF antenna is selected to be a three-dimensional ("3D") RF dipole.

Although various embodiments and methodologies have been shown and described, the disclosure is not limited to such embodiments and methodologies and will be understood to include all modifications and variations as would be apparent to one skilled in the art. For example, in yet other illustrative embodiments of the present disclosure, one or more of the inventive features described herein may be combined into a single NMR logging tool. Therefore, it should be understood that embodiments of the disclosure are not intended to be limited to the particular forms disclosed. Rather, the intention is to cover all modifications, equivalents and alternatives falling within the spirit and scope of the disclosure as defined by the appended claims.

What is claimed is:

1. A side-looking nuclear magnetic resonance ("NMR") logging tool, comprising:
    a magnet assembly to generate a static magnetic field in a volume of interest, the magnet assembly comprising at least two magnets having different directions of magnetization such that the static magnetic field results in a sensitive volume of interest where a depth of investigation in front of the logging tool is at a target depth of investigation and a depth of investigation behind the logging tool reduces a borehole signal; and
    a radio frequency ("RF") antenna to induce an RF field into the volume of interest and to receive corresponding total signals from the volume of interest, wherein:
    the RF antenna is positioned on a front side of the logging tool and the magnet assembly is positioned on a back side of the logging tool opposite the front side, and
    the RF antenna and the magnet assembly are separated from one another along an axis running from the front side to the back side of the tool.

2. A side-looking NMR logging tool as defined in claim 1, wherein the magnet assembly comprises:
    a first magnet comprising a magnetization in a first direction; and
    a second magnet comprising a magnetization in a second direction which is tilted in relation to the first direction.

3. A side-looking NMR logging tool as defined in claim 2, wherein the second direction is a tilted at an angle of 10-20 degrees in relation to the first direction.

4. A side-looking NMR logging tool as defined in claim 1, wherein the magnet assembly comprises:
    a first magnet comprising a magnetization in a first direction;
    a second magnet positioned adjacent the first magnet, the second magnet comprising a magnetization in a second direction orthogonal to the first direction;
    a third magnet positioned adjacent the second magnet, the third magnet comprising a magnetization in the second direction; and
    a fourth magnet positioned adjacent the third magnet, the fourth magnet comprising a magnetization in a third direction opposite the first direction.

5. A side-looking NMR logging tool as defined in claim 1, wherein the RF antenna is a three-dimensional ("3D") RF dipole.

6. A side-looking NMR logging tool as defined in claim 1, wherein the magnetization directions of the at least two magnets are non-diametrically arranged with respect to one another.

* * * * *